United States Patent [19]
Kelley

[11] Patent Number: 5,432,456
[45] Date of Patent: Jul. 11, 1995

[54] CONNECTOR INSTALLATION GO/NO-GO TEST FIXTURE

[75] Inventor: Randall J. Kelley, The Woodlands, Tex.

[73] Assignee: Compaq Computer Corporation, Houston, Tex.

[21] Appl. No.: 157,641

[22] Filed: Nov. 24, 1993

[51] Int. Cl.$^6$ ............................................. G01N 21/00
[52] U.S. Cl. ................................. 324/538; 356/237; 324/501
[58] Field of Search ............... 73/805.8; 356/237, 239, 356/205; 364/550; 324/538, 501

[56] References Cited

U.S. PATENT DOCUMENTS

| | | | |
|---|---|---|---|
| 3,773,426 | 11/1973 | Mudd | 356/205 |
| 4,405,233 | 9/1983 | Grau | 356/237 |
| 4,686,637 | 8/1987 | Linker | 364/550 |

*Primary Examiner*—Kenneth A. Wieder
*Assistant Examiner*—Mark Wardas
*Attorney, Agent, or Firm*—Jenkens & Gilchrist

[57] ABSTRACT

A pin protrusion test fixture includes an element having a void therethrough, structure for biasing the aforementioned element in a first direction to a first position, and structure for directing a pin toward that element so that the pin causes the element to move in a second direction to a second position. The test fixture also includes a light source and a light sensor disposed so that when the element is in the second position, light from the light source passes through the void through the element having a void therethrough and is then detected by the light sensor.

10 Claims, 1 Drawing Sheet

CONNECTOR INSTALLATION GO/NO-GO TEST FIXTURE

BACKGROUND OF THE INVENTION

FIELD OF THE INVENTION

The present invention relates to apparatus and methods for testing printed circuit boards. More particularly, the present invention relates to apparatus and methods for checking all pins of through-hole components after installation to a printed circuit board to ensure that each pin protrudes therethrough sufficiently to allow soldering.

DESCRIPTION OF RELATED ART

A wide variety of electronic devices employ printed circuit boards (PCBs). PCBs are boards for the mounting of components on which most connections are made by printed circuitry. Printed circuits (or soldered connections) are, in turn, printed wiring formed in a predetermined design in, or attached to, the surface or surfaces of a common base.

One example of a PCB is a computer motherboard. A computer motherboard is a generally rectangular component, made of plastic and strips of metal, designed to house a central processing unit (CPU) and related integrated circuits (ICs). Sockets are built into the surface of the motherboard, designed to hold the legs of the ICs. The legs, or pins, of the ICs are made of a stiff metal and they plug into IC sockets in much the same way electrical plugs slide into wall sockets.

Developments in the electronic arts have heretofore been driven in large part by a desire for components to do more while occupying less space. With respect to PCBs, this desire has caused more and more components, each with a large quantity of delicate pins, to be positioned on those boards in close proximity to each other. It is now not uncommon for a PCB to have over 1500 leads.

Notwithstanding the increased complexity caused by having more and more components attached closely together on a board, it has been and remains an important goal of PCB manufacturers to reduce, if not eliminate, defects.

Towards this goal, apparatus and methods for testing PCBs being manufactured have heretofore been developed.

One important requirement subject to testing is whether each pin of a through-hole component protrudes sufficiently through the PCB. It is important that all pins do so protrude so that good electrical contacts can be made during subsequent soldering processes. This test needs to be accurate because it is difficult to replace components once actually soldered, in whole or in part, to a board.

A prior art method of determining whether each pin of a through-hole component protrudes sufficiently through a PCB is visual inspection. During such an inspection, a board on an assembly line is picked up, turned over, and each through-hole visually checked to see if a pin is protruding through it.

The visual inspection method of testing PCBs has several defects. First, it requires considerable handling of the board, which can cause damage to delicate components. Second, the visual inspection method is time consuming. It can take quite a bit of time for a person to ensure 1,500 or more pins are protruding as required. Additionally, the visual inspection method is unreliable. Because many small delicate pins are often oriented in close proximity to each other, it is easy to miss the fact that one or more are missing or otherwise not protruding as they should.

A second method of checking all pins of through-hole components after installation to a PCB involves performance of an electrical continuity test. This test is directed to ensuring electrical continuity exists between the internal contacts of components above or on one side of the PCB and their corresponding pins below or on the other side of the PCB. Like the visual inspection test, the electrical continuity test has shortcomings and deficiencies. First, although this test can be performed in various ways, each involves physical contact with pins, which can damage them. Second, because the test does require that delicate contacts be made, which is inherently a time consuming process, performing this test increases PCB manufacturing time significantly. Third, it is not uncommon for internal contacts of components to be damaged during this test, which is wasteful and expensive.

Based upon the foregoing, those skilled in the art should understand and appreciate that it is a shortcoming and deficiency of the prior art that there has not yet been developed a quick, highly reliable, nonphysical-contact method for ensuring component pins protrude through a PCB enough to enable soldering.

SUMMARY OF THE INVENTION

The present invention overcomes the shortcoming and deficiency mentioned above by providing a pin protrusion test fixture including an element having a void therethrough, structure for biasing the aforementioned element in a first direction to a first position, and structure for directing a pin toward that element so that the pin causes the element to move in a second direction to a second position. A fixture according to the teachings of the present invention also includes a light source and a light sensor disposed so that light from the light source passes through the void in the element having a void therethrough, whereupon that light can be detected by the light sensor when the element is in the second position.

In an embodiment of the present invention there are a plurality of elements having a void therethrough, structure for biasing each of the plurality of elements, and structure for directing individual pins towards individual elements. In such an embodiment of the present invention, the voids in the elements having a void therethrough may align in at least one line when each of the elements having a void therethrough are in the second position.

In embodiments of the present invention wherein the voids in the elements having voids therethrough align in more than one line when each of the elements having a void therethrough are in the second position, there may also be structure for changing the direction of the light emitted by the light source so that it can travel through all of the voids notwithstanding the fact that they align so as to form more than one line. In embodiments of the present invention, prisms can perform the light beam direction changing function.

Further, according to the teachings of the present invention, optical fibers may be incorporated into embodiments of the present invention to facilitate light travel and control.

Accordingly, it is an object of the present invention to provide a manual assembly fixture that can perform a pin protrusion test without changing the existing assembly process.

Another object of the present invention is to provide a test fixture that can perform a pin protrusion test quickly and accurately.

Yet another object of the present invention is to provide a test fixture that can perform a pin protrusion test without inducing damage.

BRIEF DESCRIPTION OF THE DRAWINGS

Other objects, advantages, and novel features of the present invention will become apparent from the following detailed description of the invention when taken in conjunction with the accompanying drawings wherein.

DETAILED DESCRIPTION OF THE INVENTION

Figure 1:
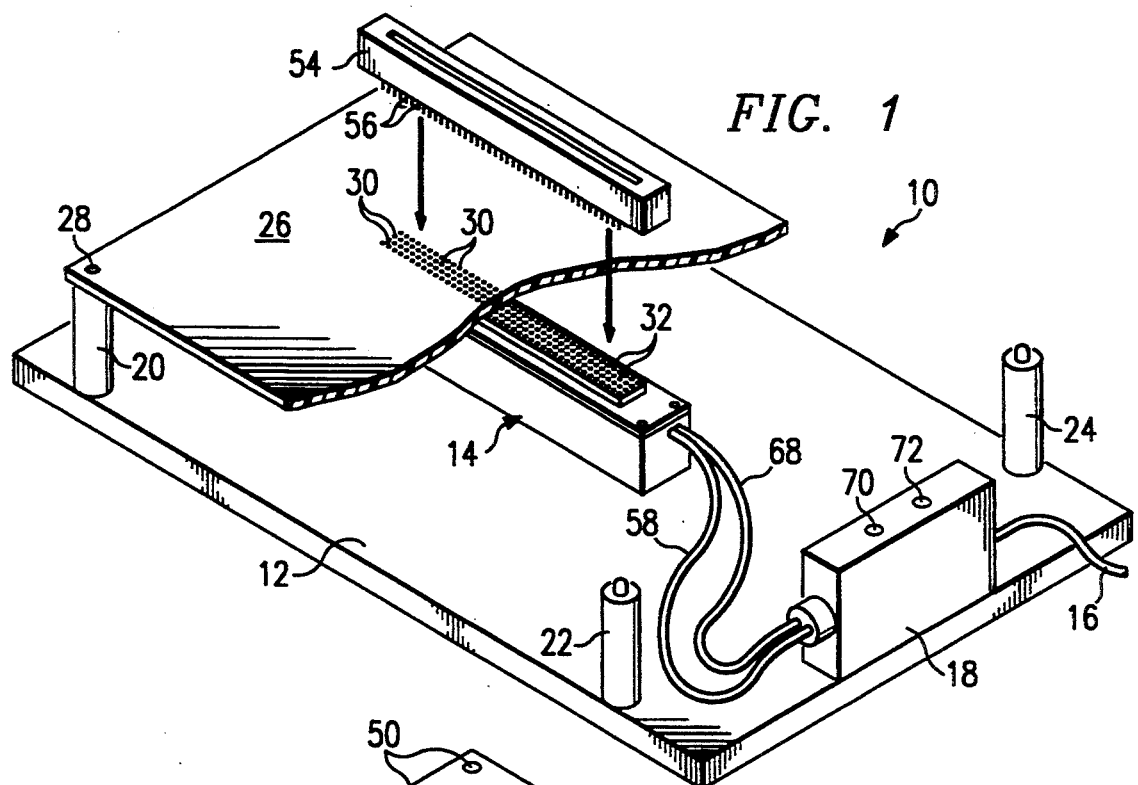
FIG. 1 is an elevated, partially cut away view of a pin protrusion test fixture according to the teachings of the present invention.

Referring now to the drawings wherein like or similar elements are depicted with identical reference numerals throughout the several views, and wherein the various components depicted are not necessarily drawn to scale, and, more particularly, to FIG. 1, there is shown an elevated, partially cut away view of a pin protrusion test fixture (generally designated by reference numeral 10) according to the teachings of the present invention. The fixture 10 may be seen in FIG. 1 to comprise a base plate 12, a test module 14, a means for supplying power 16, and a photoelectric sensor 18. Each of these components is discussed in further detail immediately below.

The base plate 12 serves as a mounting surface for the module 14 and sensor 18. The base plate 12 also serves to support tooling pins 20, 22, 24 on which a PCB 26 may be positioned (via holes 28 therethrough) in a manner so that connector through-holes 30 in the PCB 26 are aligned with holes 32 (discussed further below) in the test module 14. The base plate 12 may be formed by any one of a number of conventional materials (e.g., metal, plastic, or a combination thereof) in conventional ways. It is important, however, that the base plate 12 and tooling pins 20 be strong enough to support elements mounted or positioned thereon and to withstand repeated use. It is also important that the materials used to form the base plate 12 and tooling pins 20 not damage or interfere in any way with the testing of the PCB 26.

Figure 2:
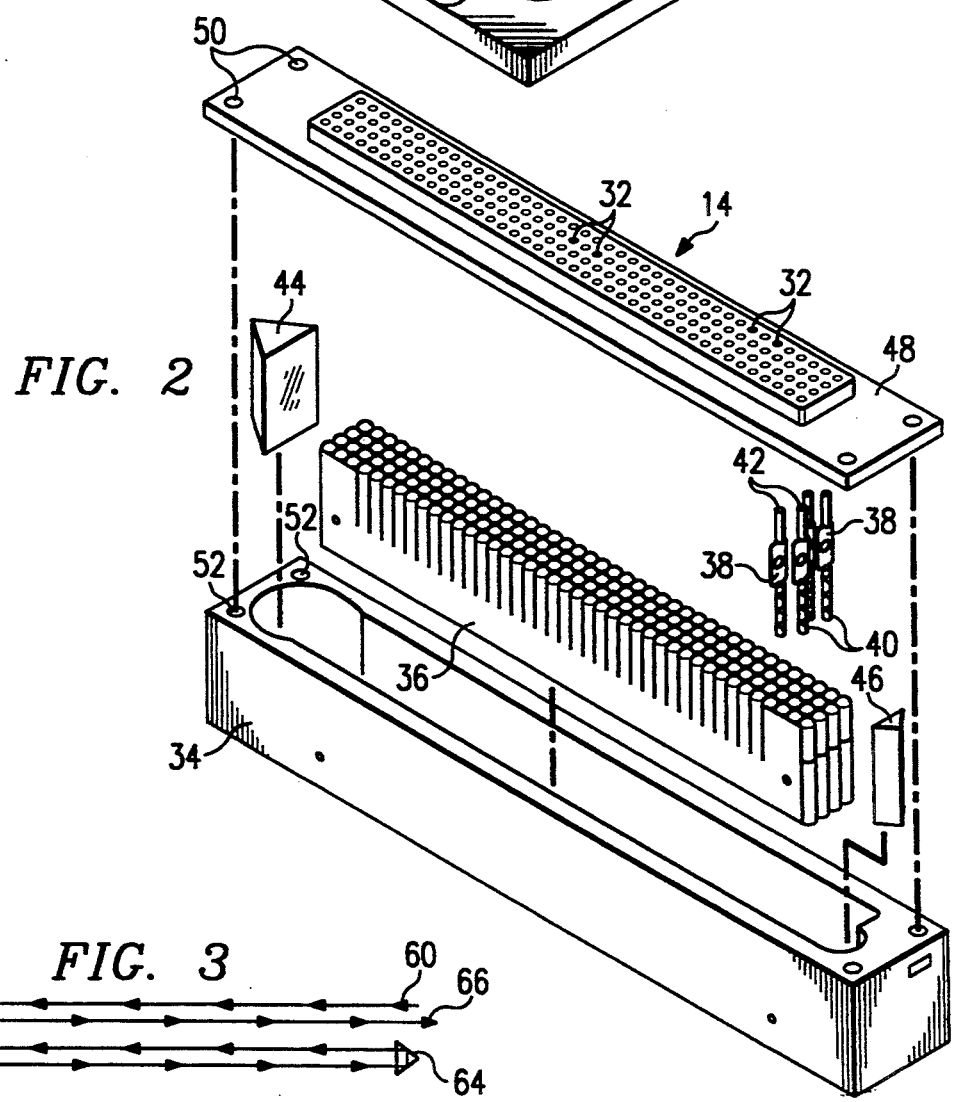
FIG. 2 is an exploded view of a portion of the test fixture depicted in FIG. 1.

The test module 14 can be better seen in FIG. 2. The module 14 shown in FIG. 2 may be seen to comprise a housing 34, a partition block 36, shutter plates 38, compression springs 40, plungers 42, prisms 44, 46 and a cover plate 48. The springs 40, shutter plates 38 and plungers 42 are serially contained in spaces in the partition block 36. A spring 40, shutter plate 38, and plunger 42 unit effectively creates an individual test cell for a component pin.

These "cells" are aligned in parallel rows by the partition block 36 to match the pin pattern of the component being tested. The entire cell and partition block 36 structure is enclosed with the housing 34 and the cover plate 48. Screw holes 56, 52 in the cover plate 48 and housing 34, respectively, provide a means whereby the test module 14 can be stably assembled.

As previously mentioned, the cover plate has holes 32 therethrough aligned with the holes 30 in the PCB. The purpose of holes 30 and 32 are to accept the pins of a through-hole component (e.g., component 54 depicted in FIG. 1) to be soldered to the PCB 26.

When the component 54 is mounted onto the PCB 26, its pins 56 project through the holes 30 and the holes 32, whereupon they impinge upon a plunger 42, shutter plate 38, and spring 40 assembly contained in a particular block cell. Assuming that all of the plungers are depressed simultaneously to the same depth (which should happen if all pins are present and uniform), the shutter plates 38 will align and effectively create a "light window". If, on the other hand, any one plunger is not depressed, a complete, unobstructed light window will not be created.

The purpose of the photoelectric sensor 18 (depicted in FIG. 1) is to determine whether an unobstructed light window exists. The sensor 18 accomplishes this by transmitting light into the test module 14. This can be accomplished by a fiber optic line 58. The sensor 18 may include means (e.g., light emitting diodes) for indicating to a fixture operator whether a light window is created. This possible aspect of an embodiment of the present invention is discussed further below.

Figure 3:
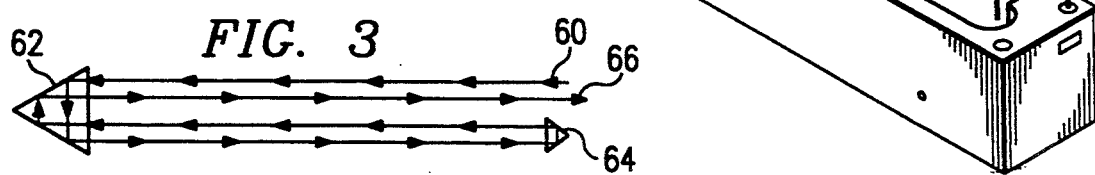
FIG. 3 is a schematic diagram showing how light could travel through an embodiment of the present invention.

Referring now to FIG. 3, there is shown the path of light through an unobstructed module 14. The light enters the module 14 at point 60 and passes through a first "light window" row (the topmost row in FIG. 3) if possible (i.e., if all shutter plates are aligned with the shutter voids on a light beam axis). At the end of this first row, the direction of the light beam is changed by a first prism 62 (or, with reference to FIG. 1, a prism 44) so that the beam reverses direction and travels down a second row (the bottommost row in FIG. 3). At the end of that row, a second, smaller prism 64 (or, again with reference to FIG. 1, a prism 46) again changes the direction of the light beam so that it travels down a third row. Similarly, the light beam may once again be modified by the first prism 62 so that the beam travels down a fourth and last row to a test module exit point 66. Referring to FIG. 1, the light, if any, exiting the test module 14 is carried via fiber optic line 68 to the sensor 18 whereupon its receipt may be detected and subsequently indicated to a test operator. Line 16 provides power to the sensor 18. If a single pin is missing, light will not be able to pass through the test module 14 and the absence of light will be noted by the sensor 18.

Based upon the foregoing, those skilled in the art should understand and appreciate how the present invention may be used. A test operator can place a PCB 26 on the tooling pins 20 and then install a through-hole component 54. The operator can then be prompted immediately by a green light emitting diode (LED) 70 or a red/green LED 72 on the sensor 18 as to whether all pins are present and the component connector is a "go" or as to whether one or more pins is missing and the component connection is a "no go", respectively.

Those skilled in the art should also understand that an embodiment of the present invention has heretofore been made and used with remarkably good results. Details recording this embodiment are set forth below:

| Springs: | OD: | .057 inch |
| --- | --- | --- |
| | Length: | .320 inch |
| | Rating: | 1 oz per inch of travel |

Fiber Optic Cable: 2½ mm diameter

The present invention provides a multitude of advantages over the prior art. The fixture can test component pins as the components are installed without changing the existing process. The operator can replace a defective part immediately prior to soldering. Use of the present invention eliminates time consuming rework of high pin count through-hole components. The present invention improves quality by testing components that are not tested by prior art means.

In addition to the foregoing, the fixture doubles as a PCB support plate. Such plates are commonly used at manual assembly points in assembly lines for through-hole components. Further, the fixture modules and sensors can be reused on new fixtures. Therefore, the cost of new fixtures can be reduced considerably.

Still further, the present invention offers the tremendous advantage of failing correctly. This ensures high result accuracy.

Obviously, numerous modifications and variations are possible in view of the teachings herein. For example, it would be possible and may even be advisable in certain applications to use an integrated plunger and aperture. Embodiments of the present invention could also include an adjustable mount for the light or means for shimming the cover plate to compensate for varying lead lengths. Other modifications and variations are possible. Accordingly, within the scope of the appended claims, the present invention may be practiced otherwise than as specifically described hereinabove.

What is claimed is:

1. A pin protrusion test fixture comprising:
   an elongated element having a void therethrough in a direction perpendicular to the direction of elongation;
   means for biasing said elongated element having a void therethrough in a first direction to a first position;
   means for directing a pin toward said elongated element having a void therethrough so that said pin causes said elongated element having a void therethrough to move to a second position;
   a light source which emits light through said void in said elongated element having a void therethrough when said elongated element having a void therethrough is in said second position; and
   a light sensor disposed so as to detect light from said light source which has traveled through said void in said elongated element having a void therethrough when said element having a void therethrough is in said second position.

2. The pin protrusion test fixture as recited in claim 1, comprising a plurality of said elongated elements, each having a void therethrough;
   a plurality of means for biasing said plurality of said elongated elements; and
   a plurality of means for directing pins toward said plurality of said elongated elements.

3. The pin protrusion test fixture as recited in claim 2, wherein said voids in said elongated elements align in at least one line when each of said elongated elements are in said second position.

4. The pin protrusion test fixture as recited in claim 2, wherein said voids in said elongated elements align in a plurality of lines when each of said elongated elements are in said second position.

5. The pin protrusion test fixture as recited in claim 4, further comprising means for changing the path of light emitted by said light source so that said light travels through said plurality of lines.

6. The pin protrusion test fixture as recited in claim 5, wherein said means for changing comprises a prism.

7. The pin protrusion test fixture as recited in claim 2, further comprising a housing, said housing containing said plurality of elongated elements, said plurality of means for biasing, and said plurality of means for directing.

8. The pin protrusion test fixture as recited in claim 7, wherein said housing has at least two voids therethrough, a first void for admitting light and a second void for allowing light to exit.

9. The pin protrusion test fixture as recited in claim 8, further comprising a first optical fiber connecting said light source and said first void, and a second optical fiber connecting said light sensor and said second void.

10. The pin protrusion test fixture as recited in claim 1, further comprising means for indicating to a fixture operator when said light sensor detects light having traveled through said void in said elongated element.

* * * * *